United States Patent [19]

Clayman

[11] Patent Number: 5,152,278
[45] Date of Patent: Oct. 6, 1992

[54] SURGICAL ENDOSCOPE APPARATUS

[75] Inventor: Ralph V. Clayman, St. Louis, Mo.

[73] Assignee: Applied Medical Resources, Inc., Laguna Hills, Calif.

[21] Appl. No.: 573,880

[22] Filed: Aug. 28, 1990

[51] Int. Cl.⁵ .............................. A61B 1/12
[52] U.S. Cl. ............................ 128/4; 128/6
[58] Field of Search .................... 128/3-8, 128/10, 11, 15, 16

[56] References Cited

U.S. PATENT DOCUMENTS

| | | | |
|---|---|---|---|
| 2,779,327 | 1/1957 | Baker | 128/6 |
| 3,261,350 | 7/1966 | Wallace | 128/6 |
| 4,103,680 | 8/1978 | Yoon | 128/6 |
| 4,561,427 | 12/1985 | Takada | 128/4 |
| 4,807,595 | 2/1989 | Hiltebrandt | 128/4 |
| 4,881,524 | 11/1989 | Boebel et al. | 128/6 |
| 4,998,527 | 3/1991 | Meyer | 128/6 |
| 5,020,514 | 6/1991 | Heckele | 128/4 |

FOREIGN PATENT DOCUMENTS 2215210  9/1989  United Kingdom ............ 128/4

Primary Examiner—Stephen C. Pellegrino
Assistant Examiner—Ralph A. Lewis
Attorney, Agent, or Firm—Richard L. Myers

[57] ABSTRACT

An endoscope is provided through which diagnostic, therapeutic or surgical apparatus can be inserted. The endoscope includes a tubular body having an eyepiece at its proximal end portion of a catheter structure and fiber optics extending from its distal end portion. An image at a distal end of the fiber optics is viewable through the eyepiece. A side tube has its distal end portion attached to the tubular body and has its proximal end portion extending towards that of the tubular body.

The lumen of the side tube serves for inserting surgical apparatus via said catheter structure into a body cavity, opening or conduit. The side tube and the tubular body define a bisecting plane which substantially bisects the tubular body. A reference plane is perpendicular to the bisecting plane and passes through a longitudinal axis of the tubular body. A handle extends generally on an opposite side of the reference plane from the side tube. The handle includes a back-of-hand engaging portion extending generally along and spaced apart from the tubular body, whereby an operator's hand fits between the tubular body and the handle with the palm of the hand against the tubular body and with the back of the hand against the back-of-hand engaging portion of the handle. Thus, the operator's fingers can position diagnostic, therapeutic or surgical apparatus through said catheter structure.

29 Claims, 2 Drawing Sheets

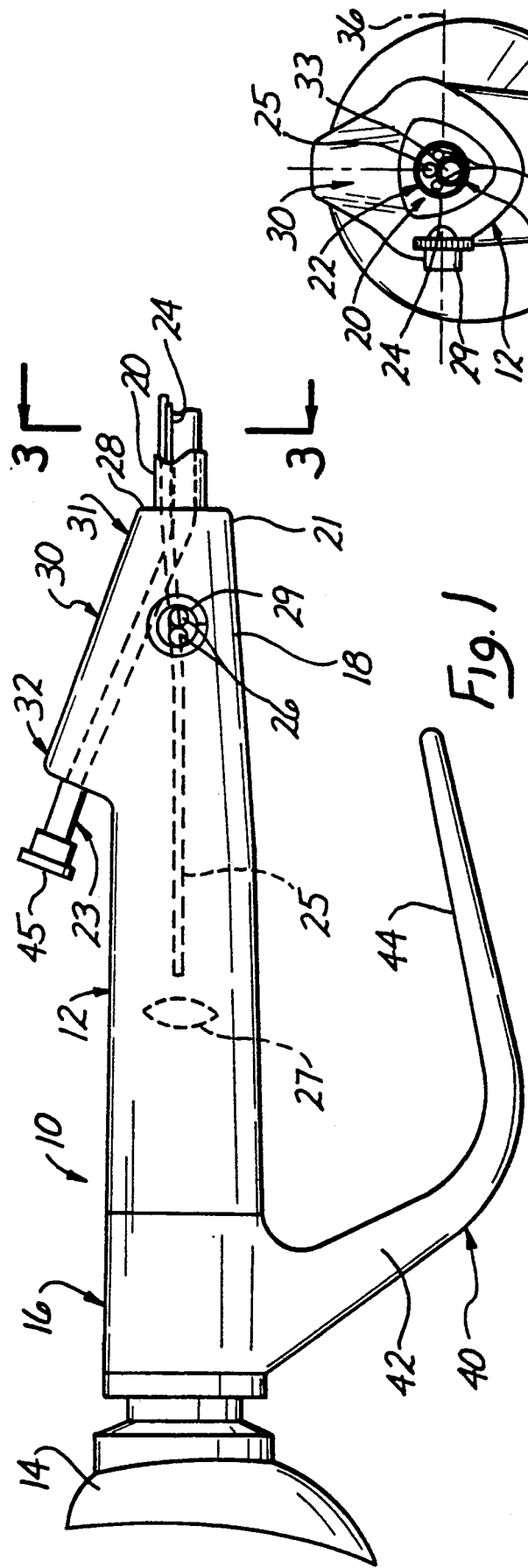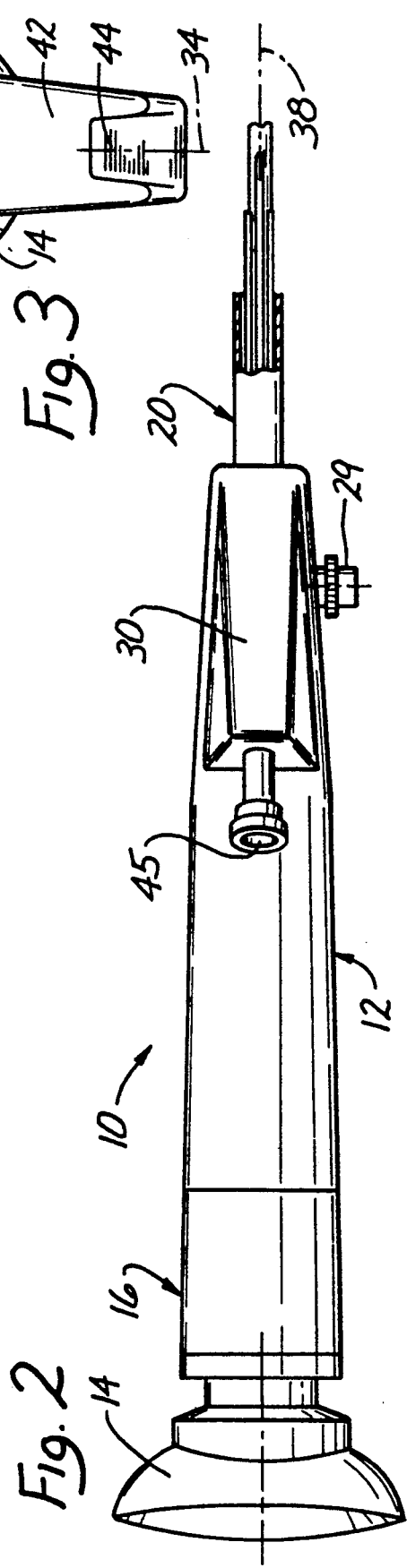

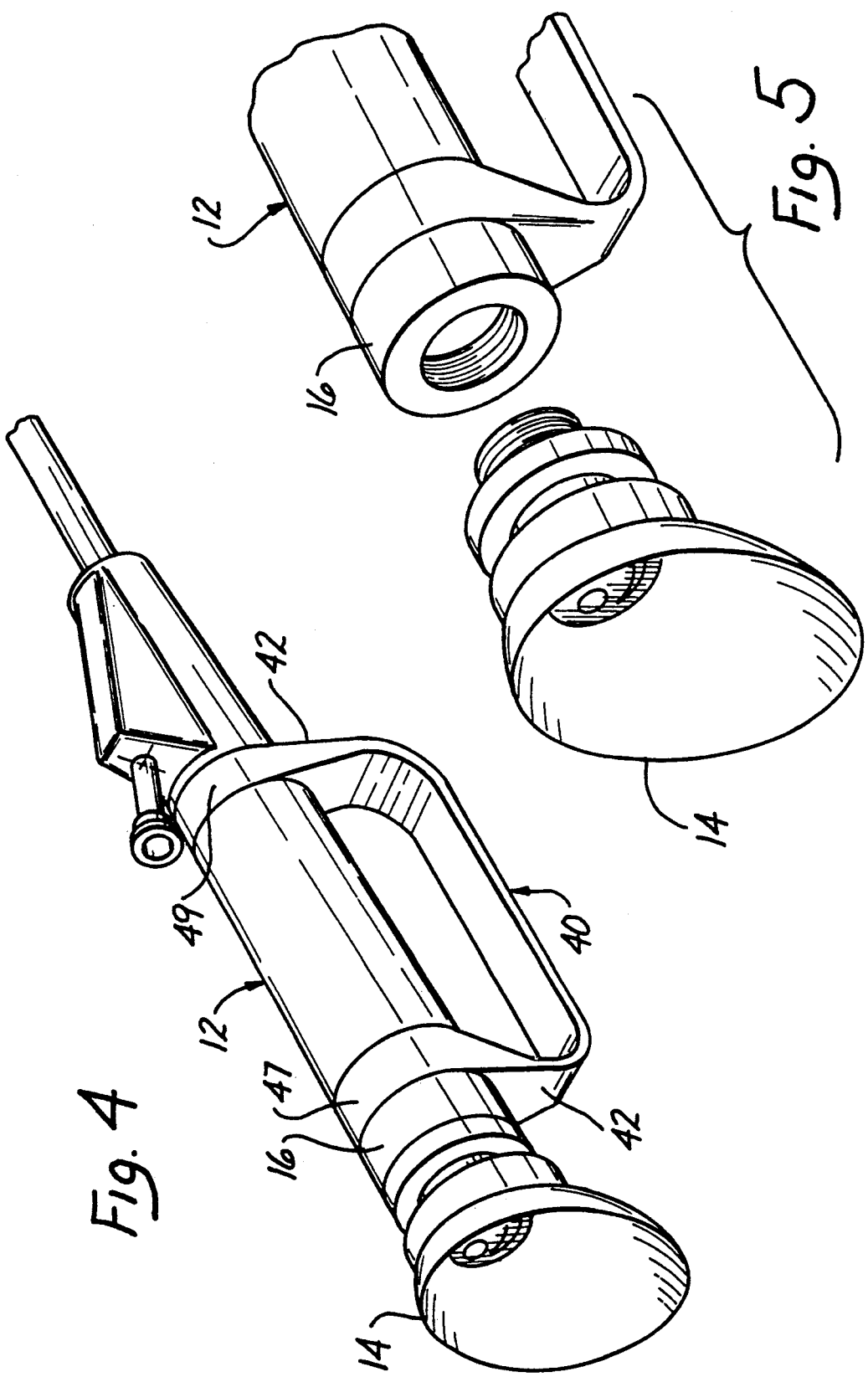

5,152,278

SURGICAL ENDOSCOPE APPARATUS

TECHNICAL FIELD

The present invention relates to an endoscope through which apparatus such as fluid introduction tubes, cutters, balloons, irrigators, aspirators and the like can be inserted. Endoscopes are useful for performing many surgical, diagnostic and therapeutic procedures.

BACKGROUND OF THE INVENTION

Use of endoscopes which allow the viewing of a surgical site within a body orifice, opening or conduit and through which surgical apparatus such as cutting elements, balloons and aspirators can be passed is relatively well known. However, with one hand holding the scope it is generally difficult or impossible for the surgeon to perform any function or manipulation that requires two hands. Such manipulations include the injection of contrast agents and adjustment of instruments or devices or the positioning and insertion of devices through the working channel of the scope.

Moreover, scopes are designed with rigid round eyepieces intended to provide attachment to other optical equipment (such as video cameras or beam splitters) as well as to match the user's eye for direct visualization. The rigid round eyepieces when used for direct visualization lack the flexibility and shape to conform to the contours or the user's face to preclude stray ambient light from distracting the user and interfering with the image. This condition often leads users to resort to dimming the lights in the operating room to minimize this effect.

The present invention is directed to overcoming one or more of the problems as set forth above.

DISCLOSURE OF INVENTION

In accordance with an embodiment of the present invention an endoscope is set forth through which surgical apparatus can be inserted. The endoscope comprises a tubular body having an eyepiece at a proximal end portion. A catheter tube, which may be rigid or flexible, extends from distal end portion of the tubular body and is adapted to be fed into a body orifice, opening or conduit. A visualization fiber bundle and light source bundle extend from the distal end of the tubular body, and are insertable via the catheter into the body cavity, opening or conduit. An image which is being observed at the distal end of the fiber optics is optically viewable through the eyepiece of the tubular body.

In accordance with the present invention a side tube carries an inner cannula which defines a working channel, the tube having a distal end portion attached to the tubular body and a proximal end portion extending towards the proximal end portion of the tubular body. The side tube has a lumen through which surgical apparatus can be inserted via the working channel of the inner cannula and via the catheter to the body cavity, opening or conduit.

The side tube and the tubular body generally define a bisecting plane which substantially bisects the tubular body. A reference plane is defined by a longitudinal axis of the tubular body and by the requirement that it be perpendicular to the bisecting plane. A handle is provided at a desired angle relative to the bisecting plane, the handle generally extending along the bisecting plane in a direction on an opposite side of the reference plane from the working channel tube. The handle has an attaching portion extending from the tubular body generally away from the tubular body a selected distance and a back-of-hand engaging portion extending generally along and spaced apart from the tubular body. The selected distance is such that an operator's hand fits between the tubular body and the handle with the palm of the hand against the tubular body, and with the back of the hand against the back-of-hand engaging portion of the handle. In this manner the operator's fingers are properly positioned and free to feed, withdraw or position surgical, diagnostic or therapeutic apparatus through the entrance port to the working channel of the inner cannula.

The present invention provides an endoscope whereby a single hand of the operator can be used to support the endoscope and the fingers of that hand can be utilized to feed surgical apparatus into, withdraw such apparatus from, or position such apparatus within a body cavity, opening or conduit. In this manner the surgeon's other hand is free to adjust equipment while the surgeon's eye is held against the eyepiece viewing the positioning of the surgical apparatus. Thus, for example, the surgeon can view a hidden surgical site and advance, withdraw and/or position surgical, diagnostic or therapeutical apparatus utilizing a single hand while viewing the site until the apparatus is in a desired position. At the same time his or her other hand is left free to activate the surgical apparatus, for example to turn on the current to an electrosurgical radio frequency cutter, to inflate a balloon, or to turn on suction and/or irrigation to clear the viewing field. In a particular embodiment, optimal disposition of the side tube and a preferred construction of the handle provides these synergistic advantages.

In accordance with a preferred embodiment of the invention the endoscope includes a detachable flexible eyepiece which is ergonomically designed to conform to the contours of the human face and to thereby provide insulation from stray ambient light. The detachable eyepiece is mounted on a rigid round eyepiece support. This allows the scope to be coupled to optical equipment by simply detaching the flexible eyepiece and coupling the optical equipment to the rigid support. Thus, the problem of stray ambient light is alleviated without limiting the use of the scope with other optical equipment.

BRIEF DESCRIPTION OF THE DRAWINGS

The invention will be better understood by reference to the figures of the drawings wherein like numbers denote like parts throughout and wherein:

FIG. 1 illustrates, in side elevation, an endoscope in accordance with an embodiment of the present invention;

FIG. 2 illustrates, in plan view, the embodiment of FIG. 1;

FIG. 3 illustrates a view taken along the line 3—3 of FIG. 1;

FIG. 4 illustrates, in a perspective view partially in section, an embodiment wherein the handle of the endoscope is rotatably mounted to its tubular body; and FIG. 5 illustrates, in a partial exploded view, a removable, rotatable eyepiece which may be adapted for use with the endoscope of the present invention.

BEST MODE FOR CARRYING OUT INVENTION

The term endoscope when used herein is used broadly to include substantially any scope which is utilized to view the interiors of body cavities, openings or conduits. Thus, this term includes other "scopes" such as cytoscopes, ureteroscopes, arthrascopes, laparoscopes, resectoscopes and the like.

An endoscope 10 in accordance with an embodiment of the present invention is illustrated in each of FIGS. 1-3 is of the nature whereby various surgical materials or apparatus (not illustrated), can be inserted and manipulated for both diagnostic and therapeutic purposes. Such materials and apparatus may include, for example, x-ray or ultrasonic contrast agents, pharmaceuticals, cutting elements, balloons, irrigation tubes, suction apparatus, and the like.

The illustrated endoscope 10 includes a tubular body 12 having an eyepiece 14 disposed at a proximal end portion 16. FIG. 3 shows an end view of the tubular body 12 with the body 12 in a desired shape for easy gripping by the palm of the operator's hand (not shown). Basically, the length of the tubular body 12 sits across the operator's hand with the thumb portion of the hand nearest the eyepiece 14. Thus, a distally narrowing or tapering lower lobe 18 of the tubular body 12 sits in the natural crease of the hand. If desired, the tubular body 12 can instead be circular in cross-section, triangular, or any other desired shape.

In accordance with the present invention a catheter tube structure 20 extends from a distal end portion 21 of the tubular body 12 and is adapted to be fed into a body orifice, opening or conduit. The catheter structure 20, illustrated in cross-section in FIG. 3, includes an outer cannula 22 and an inner cannula 23. Fiber optics 24, which include a visualization bundle 25, light source bundles 26 and a lens 27. The fiber optics 24 which are insertable via the catheter structure 20 into the body opening or conduit, are located in the space between the outer cannula 22 and the inner cannula 23. An image at a distal end of the fiber optics 24 is optically viewable through the eyepiece 14. A side hole 29 provides access for connecting the light source bundles 26 to a light source (not shown).

A side tube 30 is provided which has a distal end portion 31 thereof attached to the tubular body 12, generally to the distal end portion 21 of the tubular body 12. In a preferred embodiment, the side tube 30 is integrally molded with the tubular body 12. A proximal end portion 32 of the side tube 30 extends generally in the direction of the proximal end portion 16 of the tubular body 12. The side tube 30 defines a lumen in which the inner cannula 23 is positioned. It is this cannula 23 which provides a working channel 33 through which surgical apparatus can be inserted via the catheter structure 20. The side tube 30 and the tubular body 12 generally defines a bisecting plane 34 (see FIG. 3) which substantially bisects the tubular body 12. A reference plane 36 extends through an axis 38 of the catheter 20 and distal end 21, generally perpendicular to the bisecting plane 34.

In accordance with the present invention, a handle 40 is provided which facilitates not only the operative disposition of the tubular body 12, but also insertion and manipulation of the side tube 30. In the illustrated embodiment, the handle 40 is attached to the tubular body 12 generally at the proximal end portion 16 associated with the eyepiece 14. The handle 40 extends outwardly from the tubular body 12 and then distally toward the catheter 20. The distal end of the handle 40 is not attached to the tubular body 12 in this embodiment. Thus the handle 40 includes an attaching portion 42 which extends generally outwardly from the tubular body 12 and a back-of-hand engaging portion 44 which extends distally from the outermost region of the attaching portion 42 This disposition is preferred since the back-of-hand engaging portion 44 extends along but spaced from the tubular body 12. In the illustrated embodiment the handle is disposed generally in the bisecting plane 34 and on the side of the referenced plane 36 opposite the side tube 30.

In the illustrated embodiment, the handle 40, proximal end 16, and eyepiece 14 are pivotal relative to the tubular body 12. This feature permits adjustment of the handle 40 and particularly the back-of-hand portion 44 to provide the most comfortable fit for a particular hand size. This also permits the handle 40 to be adapted for both left handed and right handed use.

In accordance with a preferred embodiment of the present invention the attaching portion 42 of the handle 40 extends from the proximal end portion 16 of the tubular body 12. The back-of-hand engaging portion 44 of the handle 40 proceeds distally along and spaced apart from the tubular body 12. In the embodiment illustrated, the back-of-hand engaging portion 44 extends inwardly toward the tubular body 12 with progressive positions distally from the attaching portion 42 of the handle 40. As an alternative the handle 40 can be attached at each of its ends to the tubular body 12. Also, the handle can be made adjustable to fit different size hands, for example, by using a belting arrangement such as overlapping Velcro ® members.

In operation the surgeon grasps the tubular body 12 with the web of his or her hand against the attaching portion 42 of the handle 40, and with the palm of the hand receiving the tapered lobe 18 of the tubular body 12 along the natural crease which runs across the hand. With this orientation the back-of-hand, engaging portion 44 rests against the back of the surgeon's hand with the fingers and thumb reaching around the tubular body 12 in position to manipulate diagnostic, therapeutic or surgical apparatus through the working port 45. This leaves the surgeon's other hand free to manipulate other equipment. Furthermore, the surgeon can easily look through the eyepiece 14 of the endoscope 10 while performing these other tasks. Thus, both viewing through the eyepiece 14 and manipulation of instruments through the working port 45 can be accomplished simultaneously during surgery.

FIG. 5 illustrates an eyepiece 14 which is made of a flexible elastomeric material capable of conforming to the user's face contours. This is advantageous in that it eliminates stray light which can interfere with the clarity of the image observed by the surgeon. The embodiment of FIG. 5 also shows the eyepiece 14 as being removable from the proximal end portion 16 of the tubular body 12. When the eyepiece 14 is so removed other optical apparatus, for example a video camera (not shown), can be attached to the proximal end portion 16 of the tubular body 12.

INDUSTRIAL APPLICABILITY

The present invention provides an endoscope 10 useful for carrying out, among other things, resectioning within a body cavity, opening or conduit with continuous observation by the surgeon.

While the invention has been described in connection with specific embodiments thereof, it will be understood that it is capable of further modification. It is intended that the invention concept cover all variations, uses, or adaptations of the invention following, in general, the principles of the invention and including such departures from the present disclosure as come within known or customary practices in the art to which the invention pertains. It is for this reason that the scope of the invention should be ascertained only with reference to the following claims.

I claim:

1. An endoscope through which surgical apparatus can be inserted, comprising:
   a tubular body having a proximal end portion and a distal end portion;
   a catheter structure extending from the distal end portion of said tubular body and being adapted to be fed into a body orifice, opening or conduit;
   fiber optics extending form said distal end portion of said tubular body into said catheter structure, said fiber optics including a visualization fiber bundle and illuminating fibers and being insertable via said catheter structure into said body cavity, opening or conduit
   a side tube having a distal end portion thereof attached to the distal end portion of said tubular body and having a proximal end portion extending proximally toward said proximal end portion of said tubular body, said side tube having a lumen through which surgical apparatus can be inserted via said catheter structure into said body cavity, opening or conduit; and
   a handle extending generally in a distal direction on a side of said tubular body opposite said side tube, said handle having an attaching portion extending from said proximal end portion of said tubular body a selected distance and a back-of-hand engaging portion extending generally along and spaced apart from said tubular body, said selected distance being such that an operator's hand fits between the tubular body and the handle with the palm of the hand against the tubular body and with the back of the hand against the back-of-hand engaging portion of the handle whereby the operator's fingers are properly positioned and free to manipulate apparatus through said catheter structure.

2. An endoscope as set forth in claim 1, wherein said back-of-hand engaging portions extends toward said tubular body with progressive distal portions along said handle.

3. An endoscope as set forth in claim 2, wherein said tubular body has a cross-section with the general shape of a triangle to facilitate easy gripping by the palm of the operator's hand.

4. An endoscope as set forth in claim 1, wherein said tubular body has a cross-section shaped for easy gripping by the palm of the operator's hand.

5. An endoscope as set forth in claim 1, wherein said handle and said side tube extend generally in a common plane.

6. An endoscope as set forth in claim 5 wherein said back-of-hand engaging portion extends closer to said tubular body as it proceeds distally from said attaching portion of said handle.

7. An endoscope as set forth in claim 6, wherein said tubular body has a cross-section shaped for easy gripping by the palm of the operator's hand.

8. An endoscope as set forth in claim 5, wherein said tubular body has a cross-section shaped for easy gripping by the palm of the operator's hand.

9. An endoscope as set forth in claim 5, wherein said tubular body has a cross-section which tapers from the proximal end portion to the distal end portion to provide easy gripping of the palm of the user.

10. An endoscope as set forth in claim 1, wherein said back-of-hand engaging portion extends closer to said tubular body as it proceeds distally from said attaching portion of said handle.

11. An endoscope as set forth in claim 10, wherein said tubular body has a cross-section shaped for easy gripping by the palm of the operator's hand.

12. An endoscope as set forth in claim 10, wherein said handle and said side tube extend generally in a common plane.

13. An endoscope as set forth in claim 12, wherein said tubular body has a cross-section shaped for easy gripping by the palm of the operator's hand.

14. An endoscope as set forth in claim 12, wherein said tubular body has a cross-section which tapers from the proximal end portion to the distal end portion to provide easy gripping by the palm of the operator's hand.

15. An endoscope as set forth in claim 10, further comprising a flexible eyepiece having properties for conforming to the contours of a human face, the eyepiece being detachably attachable to the proximal end portion of the tubular body, and wherein the proximal end portion of the tubular body, when the eyepiece is detached therefrom, is adapted for coupling to other optical equipment.

16. An endoscope as recited in claim 10 wherein the proximal end portions include a coupling for alternative attachment to an eyepiece and a camera.

17. An endoscope as set forth in claim 1, wherein said tubular body has a cross-section which tapers distally to provide easy gripping by the palm of the operator's hand.

18. An endoscope as set forth in claim 1 wherein the proximal end portion includes a coupling for alternative attachment to an eyepiece and a camera.

19. An endoscope having a distal end and a proximal end, the endoscope being configured to be held in the hand of a user and adapted for disposition in and visualization of a body cavity, comprising:
   an operative assembly disposed at the proximal end of the endoscope and adapted for operative disposition exteriorly of the cavity;
   a body member included in the operative assembly and having a longitudinal axis, the body member being configured to fit in the palm of the hand;
   a catheter assembly disposed distally of the operative assembly and having a reduced cross-section suitable for disposition in the cavity;
   portions of the body member and the catheter assembly defining a visualization channel extending between the proximal end and the distal end of the endoscope to facilitate viewing of the cavity from a position exterior of the cavity; and
   a handle included in the operative assembly and having an attachment portion coupled to the body member and a free end portion extending longitudinally of the attachment portion and in sufficient proximity to the body member that when the palm of the hand engages to body member, the free end portion of the handle contacts the back of the hand.

20. The endoscope recited in claim 19 wherein the attachment portions of the handle are coupled to the body member and pivotal with respect to the longitudinal axis of the body member.

21. The endoscope recited in claim 19 wherein the body member is tapered distally along the longitudinal axis.

22. The endoscope recited in claim 21 wherein the free end portion of the handle extends distally, inwardly toward the longitudinal axis of the body member.

23. The endoscope recited in claim 19 wherein the free end portions of the handle extend distally inwardly toward the longitudinal axis of the body member.

24. The endoscope recited in claim 19 wherein the operating assembly further comprises:

an eyepiece pivotally attached to the handle and disposed in visual communication with the visualization channel.

25. The endoscope recited in claim 24 wherein the visualization channel, the coupling and the eyepiece are disposed along the longitudinal axis of the body member.

26. An endoscope having a distal end and a proximal end, the endoscope being configured to be held in the hand of a user and adapted for disposition in and visualization of a body cavity, comprising:

an operative assembly disposed at the proximal end of the endoscope and adapted for operative disposition exteriorly of the cavity;

a body member included in the operative assembly and having a longitudinal axis and the general cross section of a triangle, the body member being configured to fit in the palm of the hand;

a catheter assembly disposed distally of the operative assembly and having a reduced cross-section suitable for disposition in the cavity;

portions of the body member and the catheter assembly defining a visualization channel extending between the proximal end and the distal end of the endoscope to facilitate viewing of the cavity from a position exterior of the cavity; and a handle included in the operative assembly and having an attachment portion coupled to the body member and a free end portion extending longitudinally of the attachment portion for engaging the back of the hand.

27. The endoscope recited in claim 26 wherein the attachment portions of the handle are coupled to the body member and pivotal with respect to the longitudinal axis of the body member.

28. The endoscope recited in claim 26 wherein the body member is tapered distally along the longitudinal axis.

29. The endoscope recited in claim 26 wherein the free end portions of the handle extend distally inwardly toward the longitudinal axis of the body member.

* * * * *